United States Patent [19]
Van Kampen

[11] Patent Number: 4,759,765
[45] Date of Patent: Jul. 26, 1988

[54] TISSUE AUGMENTATION DEVICE

[75] Inventor: Craig L. Van Kampen, St. Paul, Minn.

[73] Assignee: Minnesota Mining and Manufacturing Company, St. Paul, Minn.

[21] Appl. No.: 840,374

[22] Filed: Mar. 17, 1986

[51] Int. Cl.[4] .............................................. A61F 2/08
[52] U.S. Cl. ................................ 623/13; 128/92 YF; 128/92 YE; 128/334 R
[58] Field of Search ....................... 623/13, 11, 16, 18; 128/334 R, 335.5, 92 YF, 92 YE, 334

[56] References Cited

U.S. PATENT DOCUMENTS

| | | | |
|---|---|---|---|
| 4,329,743 | 5/1982 | Alexander et al. | 623/13 |
| 4,411,027 | 10/1983 | Alexander et al. | 623/13 |
| 4,467,478 | 8/1984 | Jurgutis | 623/13 |
| 4,585,458 | 4/1986 | Kurland | 128/335.5 X |

FOREIGN PATENT DOCUMENTS

WO84/4311 4/1984 PCT Int'l Appl. .

OTHER PUBLICATIONS

G. K. McPherson, Ph.D., et al., Experimental Mechanical and Histologic Evaluation of the Kennedy Ligament Augmentation Device, *Clinical Orthopaedics and Related Research*, Jun., 1985, vol. 196, pp. 186-195.

Primary Examiner—Ronald L. Frinks
Attorney, Agent, or Firm—Donald M. Sell; Carolyn A. Bates

[57] ABSTRACT

A tissue augmentation device is disclosed for use in parallel with biological tissue in the repair or reconstruction of ligaments and tendons. The device comprises at least one strap-like element formed of a stable biocompatible material and a biodegradable element connected in series with the strap-like element. The device is adapted for fixation at each end thereof to the anatomical structures connected by the ligament or tendon.

16 Claims, 2 Drawing Sheets

TISSUE AUGMENTATION DEVICE

FIELD OF THE INVENTION

This invention relates to methods and devices for augmenting or reinforcing biological tissue used in the repair or reconstruction of ligaments and tendons.

BACKGROUND ART

Current methods for ligament reconstruction often involve tissue transfer procedures, wherein a tissue is transplanted from one part of the body to the site of the damaged ligament in order to reconstruct the damaged ligament. An example of such a procedure in the knee is the reconstruction of the anterior cruciate ligament by using a portion of the patellar tendon. Other tendons such as the semitendinosus tendon, and connective tissues such as fascia lata, are sometimes used to reconstruct the damaged ligament.

A problem associated with these methods for ligament reconstruction relates to the loss of strength of the transferred tissue in the early post-operative healing period. These tissues lose strength because their normal blood supply is disrupted by the transplantation procedure. During the healing process these transferred tissues eventually become revascularized and capable of regaining their strength. However, until the strength of the tissues is recovered, they must be protected from carrying normal loads. Therefore, these procedures are accompanied by long rehabilitation regimens.

The concept of tissue augmentation has been developed in order to protect transferred tissues used in ligament reconstruction by a mechanism of load sharing. Such load sharing is achieved by suturing an implant in parallel to the transferred tissue. An example of an augmentation device currently in clinical use is the 3M KENNEDY LAD Ligament Augmentation Device ™ (LAD), described by McPherson et al. in "Experimental Mechanical and Histological Evaluation of the Kennedy Ligament Augmentation Device", *Clinical Orthopaedics and Related Research*, June, 1985, Volume 196, pp. 186–195.

A critical aspect of tissue augmentation is the recognition that long-term remodeling of the transferred tissue depends on the tissue carrying a portion of the load. Biological tissues remodel according to the loads which they carry. Therefore, in order to develop a strong biological reconstruction, the transferred tissue must carry some of the load. This load sharing is achieved with the LAD by anchoring the LAD to bone at only one end. The other end is sutured to the transferred tissue. Thus, the load in the ligament reconstruction is carried from one bone, through the LAD, then into the transferred tissue, and finally into the other bone. If the LAD were anchored directly to bone at both ends of the device, the load would be carried from one bone to the other bone primarily through the LAD, with the transferred tissue shielded from carrying any significant load. Such stress shielding would result because the LAD consists of a material which has a greater axial stiffness than the tissue, and when two parallel members are of greatly different stiffnesses, the stiffer member will carry most of the load in proportion to the difference in stiffnesses. Excessive stress shielding may prevent optimal long term tissue reorganization.

A potential drawback with the current ligament augmentation method using the LAD relates to the fact that the entire length of the tissue is not augmented, thus leaving a possible weakness in the unaugmented region. Another drawback with the LAD is that free grafts, which are especially weak at their attachment sites, are only augmented at one of the attachment sites.

Some clinicians have attempted to overcome the aforementioned drawbacks by attaching the LAD to bone at both ends, thereby reinforcing the transferred tissue along its entire length. Then later, after some healing of the tissue has occurred, the attachment at one end is removed in a second surgical procedure in order to prevent long term stress shielding of the tissue. While some success has been achieved with this method, it involves the undesirable necessity of exposing the patient to the risks and trauma of a second surgical procedure.

SUMMARY OF THE INVENTION

According to the present invention there is provided a tissue augmentation device designed to be used in parallel with biological tissue in the repair or reconstruction of a ligament or tendon comprising: (1) at least one strap-like element formed of a stable biocompatible material having sufficient mechanical properties to support at least the working loads normally supported by the ligament or tendon and (2) a biodegradable element connected in series with the strap-like element at a terminal portion thereof. The device is adapted for fixation at each end thereof to the anatomical structures connected by the ligament or tendon, and has sufficient mechanical properties to support at least the working loads normally supported by the ligament or tendon at the time of implantation. However, the biodegradable element gradually looses its load-bearing capability after implantation, thereby gradually transferring increased loads to the biological tissue.

In the preferred embodiments of the device, the strap-like member comprises a braid of synthetic yarn, preferably polyolefin, and the biodegradable member comprises (1) a biodegradable connector connecting the terminal portions of two strap-like elements or (2) a biodegradable fastener attaching a terminal portion of the strap-like element to one of the anatomical structures connected by the device.

A further aspect of the invention relates to a method for the repair or reconstruction of a ligament or tendon comprising attaching in parallel with biological tissue the device described above, by fixing both ends of such device to the anatomical structures connected by the original ligament or tendon.

The primary advantage of this invention is to provide a tissue augmentation device that temporarily functions as a total prosthesis during the initial healing phase, but which provides long-term augmentation of the tissue. Thus, the tissue augmented with this device is protected from excessive stress during early healing, while the tissue is exposed to the necessary long-term loads that will optimize remodeling and strengthening. This is accomplished without the necessity for a second surgical procedure.

DESCRIPTION OF THE DRAWINGS

The invention may be further illustrated by reference to the accompanying drawings wherein:

Referring now to FIG. 1, a braided tissue augmentation device 10 of this invention is shown implanted in a knee. Device 10 has a tissue graft (not shown) sutured along its length. Device 10 is affixed to the femur 12 by an expandable fastener 14 which is shown in greater detail in FIG. 2.

Figure 2:
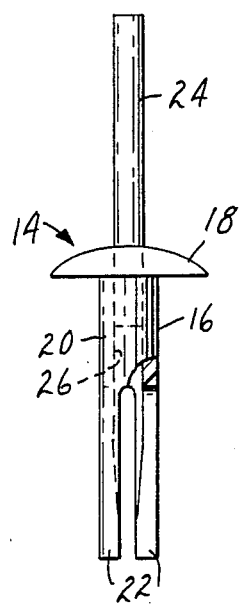
FIG. 2 is an elevational view of a fastener with parts thereof broken away.

Fastener 14 comprises: (a) receiver 16 having flanged head 18 with a central opening therein; (b) hollow cylindrical portion 20 communicating with the opening in head 18; and (c) legs 22. Post 24 is adapted for insertion into the receiver 16. Cylindrical channel 26 of cylindrical portion 20 is slightly larger in diameter than post 24 and extends through head 18, and hollow cylindrical portion 20 to legs 22. Legs 22 are biased inwardly as shown in FIG. 2 so that when post 24 is driven into the cylindrical channel 26 through head 18, and then between legs 22, legs 22 are displaced radially outward.

Figure 3:
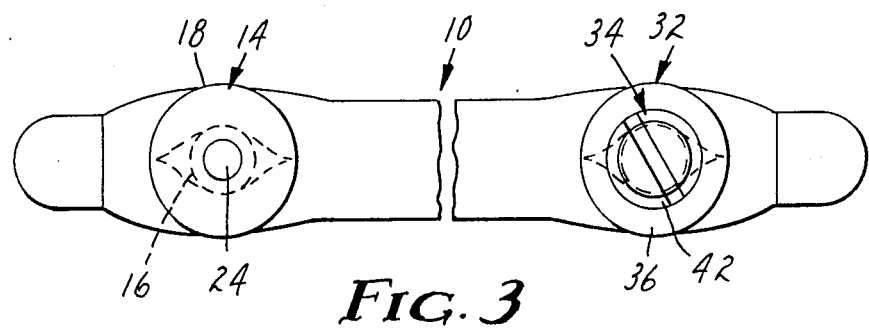
FIG. 3 is an enlarged elevational view of the device of the invention showing different fasteners at either end.

Fastener 14 is implanted by drilling a hole in the femur 12 which is only slightly larger in diameter than cylindrical portion 20 and deep enough to receive legs 22 and cylindrical portion 20. Legs 22 of the receiver 16 are inserted through the braids of one end of augmentation device 10 and a small hole created in the biological tissue. This end is shown in closer view in FIG. 3. Legs 22 are then inserted into the hole in the femur 12. The receiver 16 is then seated in the hole in the femur 12 by pressure on flanged head 18. Post 24 is then inserted in cylindrical channel 26 through flanged head 18. Post 24 is forced between legs 22 until a secure friction fit is obtained.

Figure 4:
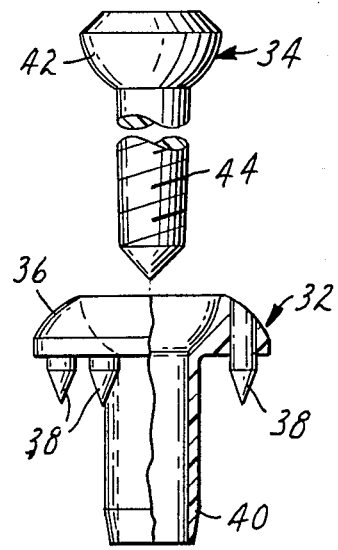
FIG. 4 is an elevational view of another embodiment of the fastener, parts thereof broken away and shown in section.

Referring again to FIG. 1, augmentation device 10 extends from fastener 14 through tibial tunnel 28. The end of augmentation device 10 opposite fastener 14 is affixed to the tibia 30 by bushing 32 and screw 34, as shown in enlarged view in FIG. 3. Screw 32 and bushing 34 are shown in FIG. 4 with a portion of bushing 32 cut away. Bushing 32 is comprised of head portion 36 having spikes 38 extending downwardly from the lower surface thereof and hollow cylindrical portion 40 integrally connected to head 36. Screw 34 has head 42 which is shaped to be seated in head 36 of bushing 32. Screw 34 is longer than bushing 32 so that threads 44 of screw 34 will extend beyond the lower end of cylindrical portion 40 of bushing 32 into the tibia 30.

Bushing 32 is implanted by inserting cylindrical portion 40 through the braids of one end of augmentation device 10 and a small hole created in the biological tissue (See FIG. 1) and then into a hole in the tibia. Screw 34 is then inserted into bushing 32 through head 36 and is bored into the tibia to securely affix augmentation device 10 to the tibia 30.

Figures 5, 6:
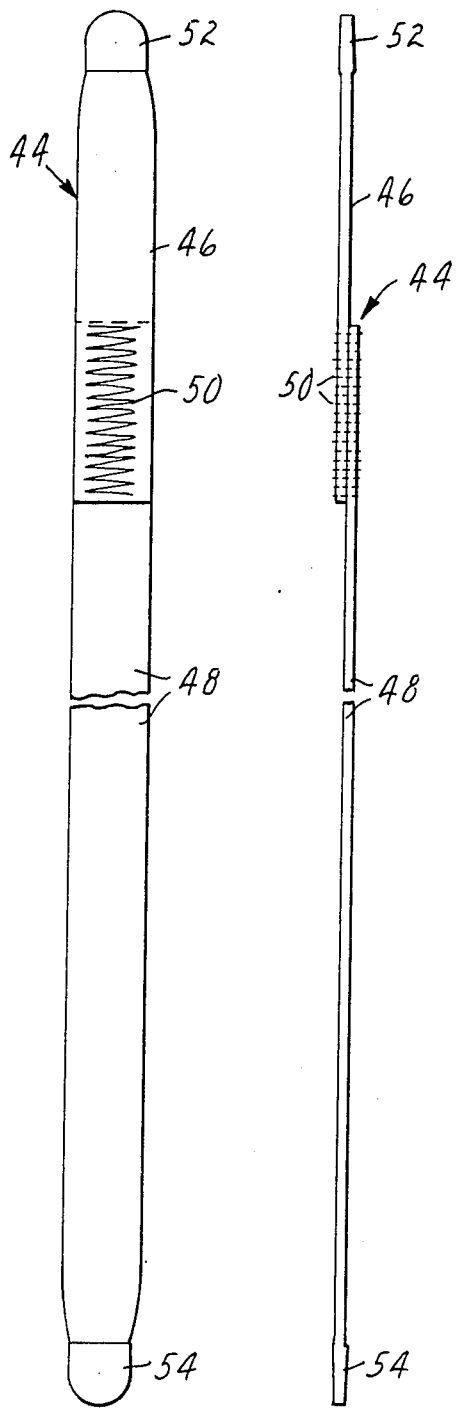
FIG. 5 is a plan view of the device of the invention showing a biodegradable suture connection.
FIG. 6 is a side elevational view of the device of FIG. 5.

In another embodiment, augmentation device 10, which consists of an integral length of braid can be replaced by the augmentation device 44 shown in FIGS. 5 and 6. FIG. 5 shows augmentation device 44 having first and second portions 46 and 48 connected by biodegradable suture 50. Free ends 52 and 54 of device 44 are heat-sealed to prevent unraveling. As can be seen from FIG. 6, first and second portions 46 and 48 are overlapped a certain amount and sewn together with biodegradable suture 50 to form a secure junction, which junction will degrade over time in the body.

Figure 1:
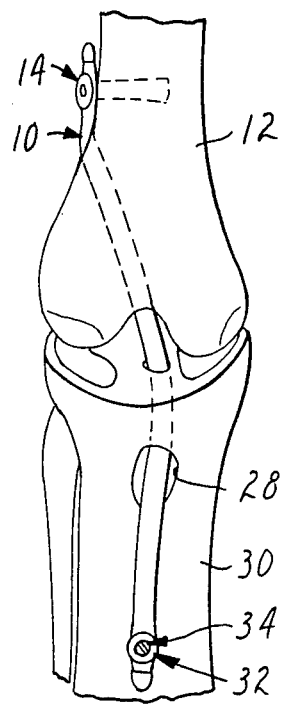
FIG. 1 is a partial view of a knee joint showing the tissue augmentation device of the invention in place.

Augmentation device 44 is preferably implanted as shown in FIG. 1 using the fastening means illustrated or any conventional fastening means.

Figure 7:
FIG. 7 is a side elevational view of an alternative connector for the device of FIGS. 5 and 6.

An alternative embodiment of augmentation device 44 can be obtained by substituting the biodegradable bobbin shown in FIG. 7 for biodegradable suture 50. Biodegradable bobbin 56 is comprised of radial flanges 58 and 60 connected by shaft 62. The diameters of radial flanges 58 and 60 are such that at least one radial flange can be inserted through the overlapping ends of first and second portions 46 and 48 of device 44 when the portions are not tensioned through their long axes, but will not slip through the respective portions when the portions are tensioned through their long axes.

At least one of the fastening means fixing the device 10 to bone must be biodegradable. The opposite end of the device may be affixed by any conventional, nonbiodegradable fastening means. This is the presently preferred method of affixing the device. However, in some cases, depending on the surgical procedure involved, it may be acceptable to use a biodegradable fastener at both ends.

With the embodiment of the device shown in FIGS. 5 and 6 having a biodegradable connector connecting two strap-like elements, conventional, nonbiodegradable fastening means may be used at both ends.

The fastening means and connectors shown in the drawings are merely illustrative. Other conventional fastening means and connectors such as rivets, staples, etc., which can be formed of biodegradable material may also be used.

The relative lengths of the two portions 46 and 48 of the device 44 of FIGS. 5 and 6 may be varied. For example, the portions may be of equal lengths as opposed to one short portion and one long portion as illustrated. Also, the two portions need not be overlapped at the connection site.

DETAILED DESCRIPTION

The device of the present invention is designed to be used in parallel with biological tissue for the repair or reconstruction of a ligament or tendon. The term "parallel" is not used in the strict geometric sense, but rather in the biomechanical sense of members sharing a common load. The augmentation device and the tissue are used adjacent to one another along their lengths, and there may be inter-twining between the two. Preferably, the augmentation device is sutured or otherwise secured to the tissue along its length. When a free tissue graft such as fascia lata is used, it is preferred to attach the device and the tissue together at each fixation site, e.g., with a common fastener.

The biological tissue used in conjunction with the device may be autogenic tissue from the patient or allogenic tissue from a donor or cadaver. In the most common ligament reconstruction practiced today, i.e., the reconstruction of the anterior cruciate ligament of the knee, the tissue used in the reconstruction is typically the patellar tendon. Other tissues such as the semitendinosus tendon, the rectus femoris tendon, and fascia lata may also be used. In the case of ligament or tendon repair, the biological tissue used in conjunction with the device of the invention is the damaged ligament or tendon itself which has been reapproximated by standard surgical techniques.

The selection of the appropriate biological tissue to reconstruct or repair a particular tendon or ligament is well within the level of ordinary skill in the field of orthopedic surgery and does not form part of the present invention. An example of a method for reconstruction of the anterior cruciate ligament using an autogenic tissue graft is the MacIntosh/Marshall method described in MacIntosh, D. L.: "Acute tears of the anterior cruciate ligament. Over-the-top repair." Presented at the Annual Meeting of the AAOS Dallas, Tex., 1974, and Marshall et al., "The Anterior cruciate ligament: A technique of repair and reconstruction." *Clin. Orthop. Rel. Res.* 143:97, 1979.

The device of the present invention comprises two essential elements: a strap-like element which provides permanent augmentation of the tissue and a biodegradable element in series with the strap-like element. The two elements in series provide a temporary total prosthesis for the ligament or tendon and shield the newly grafted or repaired tissue from excessive loads during the initial healing period.

The strap-like element may be similar to presently-known augmentation devices such as the LAD. Criteria for selection of materials for such devices are known. The term "strap-like" is used broadly to connote flexibility, and although the preferred embodiment is flat in cross-section, any cross-sectional geometry may be used.

The strap-like element must be biocompatible, i.e., it should be non-immunogenic, non-mutagenic, non-carcinogenic and elicit no chronic inflammatory response. To insure biocompatibility, it is preferred to utilize suitable biomaterials which have a proven history in implanted devices.

In addition to biocompatibility, the strap-like element must have sufficient tensile strength to carry the working loads normally carried by the ligament or tendon being repaired or reconstructed and low flexural rigidity so as to be flexible enough to prevent interference with the normal movement of the muscular or skeletal structures connected by the device.

The strap-like element must also maintain its mechanical properties over time, i.e., exhibit resistance to fatigue creep and abrasion and be stable in the moist environment of the body.

Materials which are suitable for fabricating the strap-like member, based on the foregoing criteria, generally include synthetic polymeric materials which can be formed into high strength yarns. Such polymeric materials include polyolefins such as polypropylene, ultra high molecular weight polyethylene, and polybutylene; polyesters such as polyester terephthalate; polytetrafluoroethylene; and polyaramid.

To obtain high strength and flexibility, the strap-like element is preferably fabricated from yarns of the foregoing material. Braids or weaves of these yarns are preferred.

The presently preferred braided element is identical to the LAD and consists of thirteen tows (or strands) of high tenacity (7.5 gm/denier) polypropylene yarn, with each tow containing 180 filaments. These tows are braided into a flat strap-like structure about 1.5 mm thick. The braided structure is cut to the desired length and heat sealed to prevent unraveling.

It is anticipated that a more open structure than that of the braid may offer certain advantages. A more open structure would permit viable tissue ingrowth throughout the length of the structure and even greater load sharing between the tissue and the augmentation device should be facilitated due to the ensuing mechanical interlocking.

Although polypropylene is the presently preferred material for use in the braided structure, it is anticipated that polybutylene or highly oriented ultra high molecular weight polyethylene could work as well.

The biodegradable element of the device of the invention may be formed of any material which is biocompatible, has initial mechanical properties which, when connected in series with the strap-like member, will support the working loads normally supported by the ligament or tendon being repaired or reconstructed i.e., at least about 500 Newtons and preferably at least about 750 Newtons, but which will gradually degrade over time after implantation into the body so as to gradually transfer load to the tissue.

The biodegradable element need not be absorbable so long as the requisite degradation in mechanical properties occurs and the load is gradually transferred to the tissue. Biodegradable materials for implantation into the body are well known in the biomaterials field.

Preferred biodegradable materials for use in the invention are polylactic acid (U.S. Pat. No. 3,636,956), polyglycolic acid (U.S. Pat. No. 3,297,033), polydioxanone (U.S. Pat. No. 4,052,988), poly(lactide-co-glycolide) (U.S. Pat. No. 4,137,921) and polyesteramides such as poly-(oxysuccinoyloxydodecane-1,12-di(amidocarbonylmethylene)-co-10 percent-oxysuccinoyloxy-4,9-dioxadodecane-1,12-di(amidocarbonylmethylene) and poly[oxysuccinoyloxyhexane-1,6-di(amidocarbonylmethylene)] (U.S. Pat. No. 4,343,931), and mixtures or copolymers thereof. These polymers and copolymers are preferred because they are known to be well tolerated by the body upon implantation in addition to being degradable. Mixtures of polymers allow for variation of mechanical properties.

Biodegradable elements in the form of molded plastic parts, e.g., the fastening means shown in FIGS. 2 and 4 and the connector shown in FIG. 7, are presently preferred over suture connectors because they present less surface area to the degradation forces of the body and will maintain their mechanical properties longer.

The optimum rate of degradation of the biodegradable element will vary depending upon the particular ligament or tendon being repaired or reconstructed and will have to be determined empirically. When used to reconstruct the anterior cruciate ligament of the knee, the biodegradable element should maintain sufficient mechanical properties one month after implantation so that the entire tissue augmentation device will support a load of about at least 100 Newtons. Preferably, a load of about at least 100 Newtons should be supportable after six months. The degradation should not be so slow that after two years, the entire tissue augmentation device will support a load of more than about 100 Newtons.

The degradation of the biodegradable element of the invention may be characterized by in vitro testing because the majority of biodegradable materials useful in this invention lose strength due to the simple effects of water absorption or hydrolysis. The preferred in vitro test method involves submersing devices in physiological saline baths at both body temperature and 60° C. Comparison of short-term data at these two temperatures enables determination of the acceleration effect due to increased temperature.

Specifically, this test is conducted by determining the percent strength loss after 1, 2, 3, 4, 5 and 6 weeks at both 37° C. and 60° C. Strength is measured on a tensile testing machine at a strain rate of 4%/sec. Mean strength at each time period and temperature is determined by averaging the results of 3 specimens. The percent strength loss after 6 weeks at 37° C. is given the value "S". Then the times it takes for the strength to drop $\frac{1}{3}$ S, $\frac{2}{3}$ S, and S are determined at both 37° C. and 60° C. The acceleration factor (A) due to temperature is then determined by calculating the 37° C.:60° ratio of the times at the $\frac{1}{3}$ S, $\frac{2}{3}$ S, and S levels and averaging these values. The strength of the device after 2 years at body temperature is predicted by determination of the strength after 2/A years at 60° C. For other degradable materials that might be affected by enzymatic attack or absorption of substances other than moisture, it may be necessary to use an in vitro test requiring a full 2 years to verify the degradation rate.

When the biodegradable element is a fastener for fixing one end of the strap-like element to bone, the test is carried out by affixing the fastener in a predrilled through hole in a block of stainless steel.

The device of the present invention may be used in accordance with currently practiced procedures for the repair or reconstruction of ligaments and tendons wherein biological tissue is augmented. The primary difference between the surgical implantation of the device of the present invention and that of, for example, the LAD, is that the device of the present invention augments the entire length of the tissue and is affixed at both ends to the anatomical structures connected by the ligament or tendon being repaired or reconstructed i.e., in the case of ligament repair or reconstruction the device is affixed to bone at each end, and in the case of tendon reconstruction, the device is affixed to bone at one end and to muscle or a portion of the damaged tendon near the muscle attachment at the other end. In no event is one end affixed only to the tissue being augmented. It is critical to the practice of the invention that loads are transferred initially from bone through the device to bone (or muscle in the case of tendon reconstruction or repair) with limited transfer through the tissue.

In utilizing the device of the invention, standard surgical practices such as incision location, selection of biological tissue and length, method of tissue graft harvest, graft routing and closure are utilized.

In the preferred case, the device is provided in a sterile condition to the surgeon, either as a single unit comprising two strap-like elements or segments connected by a biodegradable connector or as a kit comprising one strap-like element and one or more biodegradable fasteners such as those illustrated in FIGS. 2 and 4 to fix the strap-like element to the bone.

If use of a biological graft is preferred surgically for reconstruction, a composite graft is prepared by suturing the device to the graft tissue. Nonabsorbable sutures are used for those portions of the composite graft that will not reside in the joint space. Absorbable sutures are recommended for the area which will reside in the joint space. The device may be sutured to the tissue in either a flat manner or if enough tissue is available, the tissue may be "tubed" around the device to create a more cyclindrical structure.

The composite graft thus created is then properly positioned for implantation by the surgeon and securely fastened to the bone by mechanical means of fixation, (e.g., bushings, screws, staples, which need not be biodegradable if a biodegradable connector already exists elsewhere in the device). In the case of the reconstruction of the anterior cruciate ligament, the composite graft may first be affixed to the femur, then routed and tensioned appropriately for subsequent fixation to the tibia.

EXAMPLE 1

The two-part ligament augmentation device of the subject invention as shown in FIGS. 5 and 6 was made as a flat braid constructed from bundles or tows of polypropylene filaments. Formation of the filaments involved die extrusion of a commercial polypropylene resin into 180 filaments which were then air quenched and wrapped around winders to stretch the material and set its crystallinity. Each filament was approximately 43 microns in diameter and had a tenacity of greater than 7.5 gm/denier.

Each tow or bundle contained 180 filaments. The device was fabricated in a 6 mm width containing 9 tows of filaments. The strap-like elements were approximately 1.5 mm thick and manufactured in two segments or lengths, of 3 mm and 13 mm respectively. The demensions of the device used in this example were selected in order to allow appropriate sizing of the device for experimentation in anterior cruciate ligament reconstruction in a goat model.

The ends of the braid were heat-sealed to prevent unraveling. The two segments were connected end-to-end (non-overlapping) using four ties of 2-0 polydioxanone sutures.

The finished device is preferably ethylene oxide (ETO) sterilized (other forms of sterilization may degrade the mechanical properties of the device).

What is claimed is:

1. A tissue augmentation device designed to be used in parallel with biological tissue in the repair or reconstruction of a ligament or tendon comprising: (1) at least two strap-like elements formed of a stable biocompatible material having sufficient mechanical properties to support at least the working loads normally supported by said ligament or tendon; and (2) a biodegradable element connecting a terminal portion of one of said strap-like elements to the terminal portion of another of said strap-like elements; said device being adapted for fixation at both ends thereof to the anatomical structures connected by said ligament or tendon and having sufficient mechanical properties to support at least the working loads normally supported by said ligament or tendon at the time of implantation, and wherein said biodegradable element gradually loses its load-bearing capabililty after implantation thereby gradually transferring increased loads to said biological tissue.

2. The device according to claim 1 wherein said biodegradable element is a bioabsorbable suture.

3. The device according to claim 2 wherein said suture stitches together overlapped terminal portions of said strap-like elements.

4. The device according to claim 1 wherein said biodegradable element is a biodegradable bobbin, comprising two radial flanges spaced apart and connected by a shaft, at least one of said flanges being capable of placement through openings in both of said strap-like elements.

5. The device according to claim 1 wherein said strap-like member comprises a synthetic polymeric yarn.

6. The device according to claim 5 wherein said yarn is braided.

7. The device according to claim 6 wherein said yarn is formed into an openwork structure.

8. The device according to claim 5 wherein said polymeric yarn is selected from the group consisting of polyolefin, polyester, polytetrafluoroethylene and polyaramid.

9. The device according to claim 8 wherein said polymeric yarn is a polyolefin.

10. The device according to claim 9 wherein said polyolefin yarn is polypropylene.

11. The device according to claim 9 wherein said polyolefin yarn is polybutylene or ultra high molecular weight polyethylene.

12. The device according to claim 1 wherein said biodegradable element is bioabsorbable.

13. The device according to claim 1 wherein said biodegradable element is formed of a polymeric material selected from the group consisting of polyesteramide, polydioxanone, polylactic acid, polyglycolic acid and copolymers thereof.

14. The device according to claim 1 capable of bearing a tensile load of at least about 500 Newtons at the time of implantation.

15. The device according to claim 1 capable of bearing a tensile load of at least about 100 Newtons for one month and no longer than two years after implantation.

16. A method of repairing or reconstructing a ligament or tendon using a biological tissue in parallel with the tissue augmentation device of claim 1.

* * * * *